United States Patent
Reid et al.

(10) Patent No.: US 6,627,766 B2
(45) Date of Patent: Sep. 30, 2003

(54) USE OF PHENYLENEDIAMINES AND HINDERED PHENOLS TO INHIBIT POLYMER FORMATION DURING THE MANUFACTURE OF ACRYLONITRILE

(75) Inventors: Dwight K. Reid, Houston, TX (US); Marilyn W. Blaschke, Richmond, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 10/331,835

(22) Filed: Dec. 30, 2002

(65) Prior Publication Data

US 2003/0109739 A1 Jun. 12, 2003

Related U.S. Application Data

(62) Division of application No. 08/482,049, filed on Jun. 7, 1995.

(51) Int. Cl.$^7$ ............................................. C07C 255/08
(52) U.S. Cl. ...................................... 558/305; 558/306
(58) Field of Search ................................. 558/305, 306

(56) References Cited

U.S. PATENT DOCUMENTS

| | | | |
|---|---|---|---|
| 2,783,269 | A | 2/1957 | Bellis |
| 3,689,558 | A | 9/1972 | Modeen et al. |
| 3,821,177 | A | 6/1974 | Chan |
| 3,915,941 | A | 10/1975 | Chan |
| 4,017,544 | A | 4/1977 | Mullins |
| 4,267,365 | A | 5/1981 | Findeisen |
| 4,720,566 | A | 1/1988 | Martin |
| 4,912,247 | A | 3/1990 | Roling |
| 5,128,484 | A | 7/1992 | Kita et al. |
| 5,288,473 | A | 2/1994 | Shaw et al. |

OTHER PUBLICATIONS

S. Jena, et al., "Retardation of V5+–Cyclohexanone Initiated Polymerization of Acrylonitrile by Phenol," Journal of Macromolecular Science—Chemistry, 1983, pp. 189–199, vol. A20, No. 2.

Primary Examiner—Joseph K. McKane
Assistant Examiner—Ebenezer Sackey
(74) Attorney, Agent, or Firm—Madan, Mossman & Sriram, P.C.

(57) ABSTRACT

The present invention relates to the use of phenylenediamines, preferably para-phenylenediamines, in combination with hindered phenols, to reduce polymer formation during the manufacture of acrylonitrile.

12 Claims, 2 Drawing Sheets

USE OF PHENYLENEDIAMINES AND HINDERED PHENOLS TO INHIBIT POLYMER FORMATION DURING THE MANUFACTURE OF ACRYLONITRILE

CROSS-REFERENCE TO RELATED APPLICATION

This application is a divisional application from U.S. patent application Ser. No. 08/482,049 filed Jun. 7, 1995, now allowed.

FIELD OF THE INVENTION

The present invention relates to the use of phenylenediamines, preferably in combination with hindered phenols, to reduce polymer formation during the manufacture of acrylonitrile.

BACKGROUND OF THE INVENTION

Acrylonitrile is produced commercially in systems using what is known as the "Sohio" process, described in U.S. Pat. No. 2,904,580 to Idol. The reactor feeds in a commercial acrylonitrile system using the "Sohio" process are propylene, ammonia, and compressed air. The propylene and ammonia are vaporized, combined with the air, and fed to a fluidized bed catalytic reactor. Precise ratios of the three feeds are maintained for optimum yield.

The manufacture of acrylonitrile has four basic stages: a reaction stage, in which the ammonia and propylene are reacted; a cooling stage, in which the reaction product is cooled; an absorption stage, in which a crude acrylonitrile product is collected; and, a purification stage, in which the crude acrylonitrile product is purified.

In the reaction stage, the propylene, ammonia, and compressed air feeds are mixed together in a reactor and react on the surface of a fluidized catalyst. A set of complex exothermic reactions takes place, forming the following products: acrylonitrile, hydrogen cyanide, carbon dioxide, carbon monoxide, acetonitrile, hydrogen, acrolein, acrylic acid, water, other higher nitrites, aldehydes, ketones, acetic acid, and a number of miscellaneous unknown organic compounds. Conversion of the three feeds is less than 100%; therefore, unreacted propylene, ammonia, oxygen, and nitrogen are contained in the reactor effluent gas.

A portion of the heat produced by the exothermic reaction is removed by sets of steam coils. Reactor effluent gas passes through cyclones, which remove catalyst fines from the gas. The gas then is cooled in a reactor effluent cooler.

In the cooling stage, the gas leaving the reactor effluent cooler is cooled in a quench column by contact with a recirculating water stream. Most of the water vapor and small amounts of organic vapors in the gas are condensed in the quench column. The quench column bottoms are cooled and circulated back to the quench column. The excess quench water is roughly equal to the amount of water produced by the reactor and is fed to the wastewater column, where acrylonitrile and hydrogen cyanide are recovered. Wastewater column bottoms ultimately are injected into the wastewater injection well.

In the absorption stage, the quench column effluent gas is directed to an absorber where chilled water is used to absorb acrylonitrile, hydrogen cyanide, and other organics from the gas. Absorber bottoms are fed to a recovery column where a crude acrylonitrile product is taken overhead.

The crude acrylonitrile product then goes through a purification stage in a series of distillation columns. The first column (heads column) removes hydrogen cyanide, while the second column (drying column) removes water. The last column (product column) takes pure acrylonitrile monomer from a side-draw near the top of the column. Heavy ends are rejected from the product column bottoms.

Unfortunately, the acrylonitrile monomer can polymerize during the cooling stage in the quench column and during the purification stage in the distillation columns. The acrylonitrile that does polymerize in the quench column and/or distillation columns represents an undesirable net product loss for the acrylonitrile plant.

Inexpensive compounds that effectively inhibit the premature polymerization of acrylonitrile during its manufacture are sorely needed.

SUMMARY OF THE INVENTION

The present invention relates to the use of phenylenediamines, preferably para-phenylene diamines, preferably in combination with hindered phenols to reduce polymer formation during the manufacture of acrylonitrile.

DETAILED DESCRIPTION OF THE INVENTION

Figure 1:
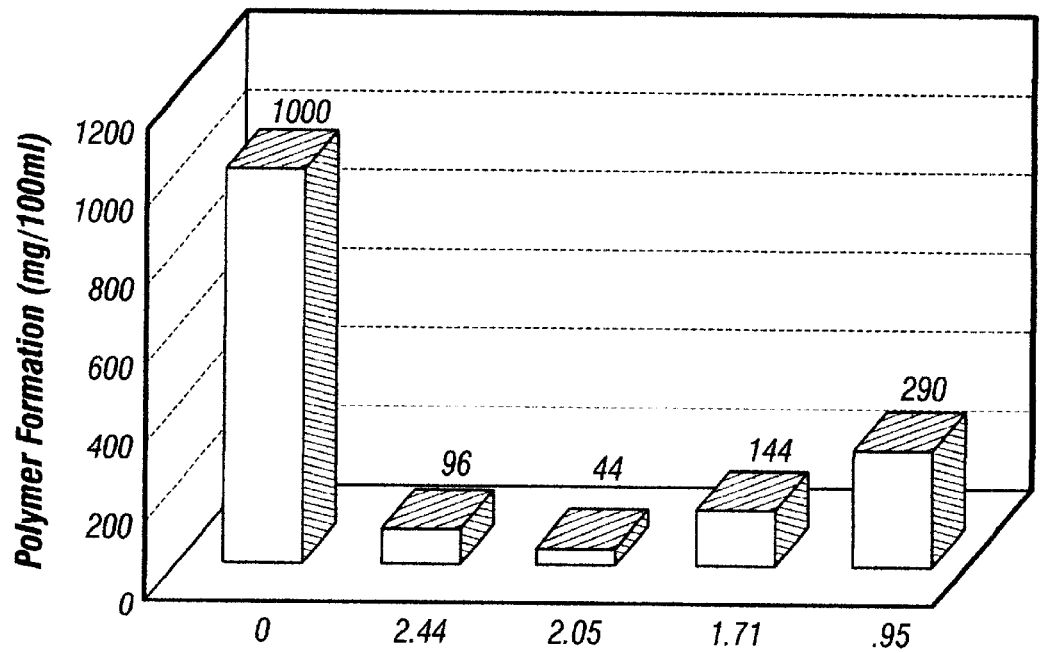
FIG. 1 is a chart showing the effect of various mixtures of BHT/NAUGAURD I-3 on polymer formation.

Preferred phenylenediamines for use in the present invention are "para-phenylenediamines" which are defined as having the following formula:

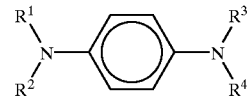

wherein $R^1$, $R^2$, $R^3$, and $R^4$ independently are selected from the group consisting of hydrogen, alkyl groups, aryl groups, alkaryl groups, and aralkyl groups, provided that at least one of $R^1$, $R^2$, $R^3$, and $R^4$ is hydrogen. The size of the substituents is limited only insofar as steric hindrance may interfere with the efficiency of the molecule as an inhibiting agent. In a preferred embodiment, the alkyl groups have between about 1–9 carbon atoms.

Examples of suitable phenylenedianines include, but are not necessarily limited to: N,N'-di(nitroso)-N,N'-di(1,4-diethylpentyl)-1,4-phenylenediamine, which is available as "MVDI" from Uniroyal Chemical Co.; N,N,N'-trimethyl-p-phenylenediamine, available from Aldrich Chemical Co. ("Aldrich"); N,N-dimethyl-p-phenylenediamine, available from Aldrich; N,N-diethyl-p-phenylenediamine, available from Aldrich; N,N'-di-sec-butyl-p-phenylenediamine, which is available as "UOP-5" from Universal Oil Products; N-phenyl-N'-dibutyl-p-phenylenediamine, available from Aldrich; N-phenyl-N'-(1,4, dimethylpentyl)-p-phenylenediamine, which is available as "NAUGARD I-3" from Uniroyal Chemical Co.; and, N-phenyl-N'-(1,3-dimethylbutyl)-p-phenylenediamine, which is available from Uniroyal Chemical Co.

Preferred phenylenediamines are para-phenylenediamines, including, but not necessarily limited to: N,N'-di(nitroso)-N,N'-di(1,4-diethylpentyl)-1,4-phenylenediamine, "MVDI," Uniroyal Chemical Co.; N-phenyl-N'-(1,4, dimethylpentyl)-p-phenylenediamine, "NAUGARD I-3," Uniroyal Chemical Co., and N,N'-di-sec-butyl-p-phenylenediamine, "UOP-5," Universal Oil Products.

In the following examples, N,N'-di(nitroso)-N,N'-di(1,4-diethylpentyl)-1,4-phenylenediamine ("MVDI"), alone, was effective in the present invention. Otherwise, the phenylenediamines of the present invention preferably are used in conjunction with a hindered phenol. The hindered phenols of the present invention are defined as having the following formula:

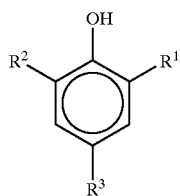

wherein $R^1$ and $R^2$ independently are selected from the group consisting of hydrogen, alkyl groups, including cyclic and heterocyclic alkyl groups, aryl groups, alkaryl groups, and aralkyl groups; and, wherein $R^3$ is selected from the group consisting of hydrogen, alkyl groups, including cyclic and heterocyclic alkyl groups, aryl groups, alkaryl groups, aralkyl groups, alkyloxy groups, and substituted or unsubstituted amino groups. The size of the substituents are limited only insofar as steric hindrance may interfere with the efficiency of the molecule as an inhibiting agent. In a preferred embodiment, the alkyl groups have between about 1–9 carbon atoms.

Preferred hindered phenols include, but are not necessarily limited to: 2,6-di-tert-butyl phenol, which is available from Aldrich; 2,6-di-tert-butyl-4-methyl phenol (BHT), which is available from Universal Oil Products; 2,6-dimethyl phenol, which is available from Aldrich; 2,4,6-tri-tert-butyl phenol, which is available from Janssen Chimica; 2,6-di-tert-butyl-4-amine phenol, which is available from Aldrich; and 2,4-di-tert-butyl phenol, which is available from Aldrich.

The preferred ratio of hindered phenol to phenylenediamine will vary according to the particular materials used. Preferably, the amount of hindered phenol should be at least about twice the amount of the phenylenediamine, preferably between about 2–2.5 times the amount of phenylenediamine. Where the hindered phenol is 2,6-di-tert-butyl-4-methyl-phenol (BHT) and the phenylenediamine is NAUGARD I-3, a preferred ratio is 2.05:1::BHT:NAUGARD I-3, respectively. Where the phenylenediamine is UOP-5, a preferred ratio is 2.47:1::BHT:UOP-5.

The phenylenediamines and hindered phenols can be added to the acrylonitrile mixture using any conventional method. The components may be added as a single composition containing the inhibitor compounds or the individual components may be added separately or in any other desired combination. Preferably, the components are added using a suitable carrier solvent which is compatible with the acrylonitrile reaction solution or vapor. Suitable carrier solvents include hydrocarbons and heavy aromatic naphthas; xylenes; toluenes; kerosine; mineral oils and acetone; alcohols, such as octanol, hexanol, and 1,4-butanediol; and, aprotic solvents, such as dimethylformamide, dimethylsulfoxide (DMSO), pyrrolidone, and N-methyl pyrrolidone.

In a preferred embodiment, the solvent should be a mixture that includes between about 5–20% by weight, preferably between about 12–18% by weight, of a cosolvent. Suitable cosolvents are organic amines, such as octylamine, cyclohexamine, butylamine, dodecylamine, and similar compounds. A preferred cosolvent is octylamine.

A most preferred embodiment contains the following:

21.85% BHT;

10.16% UOP-5;

16.10% octylamine;

51.89% FINASOL 150.

FINASOL 150 is a heavy aromatic naphtha, which may be obtained from Fina Oil.

Preferably, the phenylenediamine is injected into the reactor effluent gas downstream of the reactor effluent cooler. The total amount of phenylenediamine that is required to inhibit polymerization of acrylonitrile will vary according to the particular conditions of use. At higher temperatures, larger amounts of phenylenediamine generally will be required to inhibit polymerization. In a preferred embodiment, the amount of phenylenediamine/hindered phenol that is added should be between about 1–150 ppm, preferably between about 15–75 ppm, most preferably between about 20–50 ppm.

The invention will be better understood with reference to the following examples:

EXAMPLE 1

100 ml of acrylonitrile monomer was charged to a 250 ml three-neck round bottom flask. 50 ppm of MVDI, obtained from Uniroyal Chemical Co., was added to the acrylonitrile monomer, and withheld from controls. 200 ppm of the initiator tert-butyl hydroperoxide was added to the acrylonitrile or acrylonitrile/inhibitor solution to (a) decrease the time required for any polymerization to occur, and (b) to more closely simulate the expected environment in actual use. With the condenser attached to the reaction vessel, the monomer material was heated to reflux, and refluxed for four and one-half hours. The stressed acrylonitrile was cooled to 32° C. (90° F.), and 100 ml of n-heptane was added. The white polymer material was allowed to precipitate out of solution for 30 minutes. The liquid/polymer material then was filtered through a FisherBrand glass fiber filter paper (G6), diameter 7.00 cm (cat. No. 09-804-70A), using a Buchner funnel with vacuum. The filter paper was placed in a pre-weighed Petri-dish and dried in a vacuum oven (27–30 mmHg) at 107° C. (225° F.) for 1 hour. The Petri-dish was removed from the oven, placed in a desiccator, and cooled under vacuum (27–30 mmHg) for 1 hour. The weight of any polymer formed was determined. In the controls, between 330–440 mg of polymer formed. In the test samples containing MVDI, only 60 mg of polymer formed.

EXAMPLE 2

The materials shown in Table I were screened using the following procedures.

100 ml of acrylonitrile monomer obtained from Sterling Chemical Co., Texas City, Tex. was charged to a 250 ml three-neck round bottom flask. The indicated amount of inhibitor and any other desired material (ppm) was added to the acrylonitrile monomer. 200 ppm of the initiator tert-butyl hydroperoxide was added to the acrylonitrile or acrylonitrile/inhibitor solution.

The system was purged with nitrogen for 18 minutes, allowing all nitrogen/air to be removed through the open end of the reflux condenser. While continuing to purge, the contents of the flasks were heated to reflux 70–75° C. (158–163° F.) and held for three hours. The solution was cooled to 32° C. (90° F.) under nitrogen atmosphere. The nitrogen addition was stopped, and 100 ml of n-heptane was added.

The white polymer material was allowed to precipitate out of solution for 30 minutes. The liquid/polymer material then was filtered through a FisherBrand glass fiber filter paper (G6), diameter 7.00 cm (cat. No. 09-804-70A), using a Buchner funnel with vacuum. The filter paper was placed in a pre-weighed Petri-dish and dried in a vacuum oven (27–30 mmHg) at 107° C. (225° F.) for 1 hour. The Petri-dish was removed from the oven, placed in a desiccator, and cooled under vacuum (27–30 mmHg) for 1 hour. The weight of any polymer formed was determined and recorded. The results are given in Table I.

In the Table I, and throughout the application, "I-3" refers to NAUGARD I-3, Uniroyal Chemical Co.; "DEHA" refers to N,N-diethyl hydroxylamine, obtained from Atochem Chemical Co.; 2,6 TBp refers to 2,6-di-tert-butylphenol, obtained from Aldrich; "CHEMO T-33" refers to an imidazoline obtained from Chemtron; "ALKATERGE TIV" refers to an oxazoladine obtained from Angus Chemical Co.; "EAE" refers to 2 (N-aminoethyl) ethanol, obtained from Aldrich; "LUBRIZOL 2600" refers to a polyisobutylene succinamide, obtained from Lubrizol Corp.; and, "DMBD" refers to 3,3-dimethyl-1,2-butanediol, obtained from Aldrich.

TABLE I

| Additive | (ppm active) | [wt. polymer (mg)] |
| --- | --- | --- |
| None | — | 760 |
| BHT/I-3 | 42/25 | 44 |
| BHT/I-3 | 50/25 | 96 |
| BHT/I-3 | 35/25 | 144 |
| BHT/I-3 | 35/45 | 290 |
| DEHA/I-3 | 45/30 | 411 |
| I-3 | 75 | 158 |
| BHT/I-3 | 48/30 | 99 |
| BHT/UOP- 5 | 48/22 | 26 |
| BHT/UOP- 5 | 55/26 | 52 |
| 2,6 TBp/UOP-5 | 48/25 | 69 |
| BHT/UOP-5/Valeric acid | 48/22/10 | 48 |
| BHT/UOP-5/Soybean oil | 48/22/20 | 57 |
| BHT/UOP-5/Octylamine | 48/22/20 | 20 |
| Hydroquinone | 75 | 180 |
| BHT/UOP-5/CHEMO T-33 | 48/22/10 | 190 |
| BHT/UOP-5/ALKATERGE TIV | 48/22/10 | 58 |
| BHT/UOP-5/EAE | 48/22/15 | 16 |
| BHT/UOP-5/LUBRIZOL 2600 | 48/22/15 | 96 |
| BHT/UOP-5/octylamine | 48/22/15 | 8 |
| none | — | 783 (fresh) |
| UOP-5 | 16 | 155 |
| BHT/UOP-5 | 35/16 | 40 |
| BHT/UOP-5/Valeric acid | 35/16/20 | 47 |
| BHT/UOP-5 | 35.8/15.3 | 19.6 |
| BHT/UOP-5/DMBD | 32.8/15.3/17.5 | 40.0 |
| BHT/UOP-5 | 13/6 | 231.0 |
| BHT/UOP-5 | 17.7/8.2 | 17.0 |
| BHT/UOP-5/octylamine | 17.7/8.2/15 | 3.0 |
| BHT/UOP-5/octylamine | 176.5/82.3/150 | 28.8 |
| BHT/MEHQ | 55/32 | 62.0 |
| BHT/MEHQ | 55/15 | 137.7 |

Combinations showing some level of inhibition are functional in the present invention. Combinations resulting in the formation of 100 mg or less of polymer are preferred.

EXAMPLE 3

The following experiment was run to determine the effectiveness of hindered phenols in combination with phenylenediamines. The procedures of Example 2 were followed, using a reflux temperature of 75° C. and a reflux time of 3 hours. The test materials were 2,6-di-tert-butyl-4-methyl-phenol (BHT) and N-phenyl-N'-(1,4,dimethylpentyl)-p-phenylenediamine ("NAUGARD I-3") at the following molar ratios of BHT:I-3 in each flask: 0 (none of either BHT or I-3); 2.44 (50 ppm BHT; 25 ppm I-3); 2.05 (42 ppm BHT:25 ppm I-3); 1.71 (35 ppm BHT:25 ppm I-3); 0.95 (35 ppm BHT:45 ppm I-3). FIG. 1 is a chart of the relative effectiveness of these molar ratios.

FIG. 1 demonstrates that the molar ratio of BHT to phenylenediamine is important, and that synergism is observed at the proper molar ratios. Using BHT and NAUGARD I-3, the most effective molar ratio was 2.05.

EXAMPLE 4

The following experiment was run to determine the effectiveness of hindered phenols in combination with phenylenediamines and to compare their effectiveness with other inhibiting agents. The procedures of Example 2 were followed, using a reflux temperature of 75° C. and a reflux time of 3 hours. The test materials were: an untreated control; 75 ppm hydroquinone (HQ); 25 ppm p-nitrosophenol (PNP, another inhibitor which is covered in a separate application filed concurrently herewith); 80 ppm hydroxylamine/NAUGARD I-3 (i.e., described in U.S. Pat. No. 4,720,566); TEMPO (abbreviated herein as "TP"), an inhibitor sold by Aldrich; and, a total of 26 ppm of a combination of 18.5 ppm 2,6-di-tert-butyl-4-methyl-phenol (BHT) and 7.5 ppm N,N'-di-sec-butyl-p-phenylenediamine ("UOP-5") blended with 18 ppm octylamine.

Figure 2:
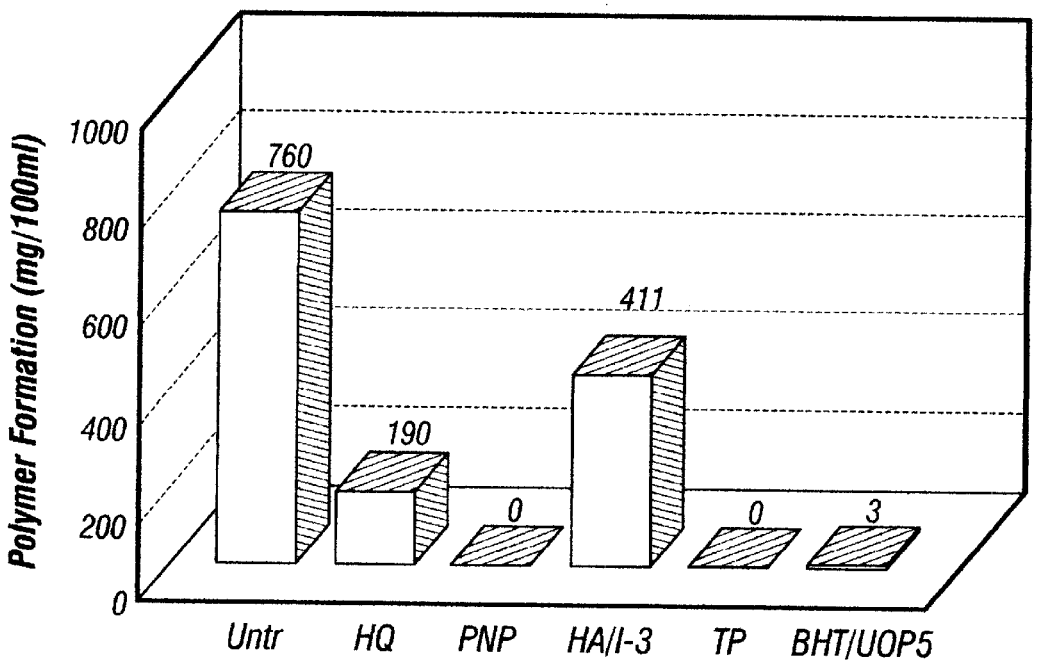
FIG. 2 is a chart showing the effect of a combination of BHT/UOP-5 compared to known polymerization inhibitors.

FIG. 2 is a chart of the relative effectiveness of these materials. The BHT/UOP-5 combination was comparable in effectiveness to p-nitrosophenol and TEMPO, and was much more effective than the hydroquinone and the combination of hydroxylamine and NAUGARD I-3.

EXAMPLE 5

The following experiment was designed to test the importance of concentration on the effectiveness of a BHT/UOP-5 combination. The procedures of Example 2 were followed using the following concentrations of the BHT/UOP-5 mixture at a molar ratio of 2.15:1: 81 ppm; 70 ppm; 48 ppm; 26 ppm; 26 ppm; and, 17 ppm.

Figure 3:
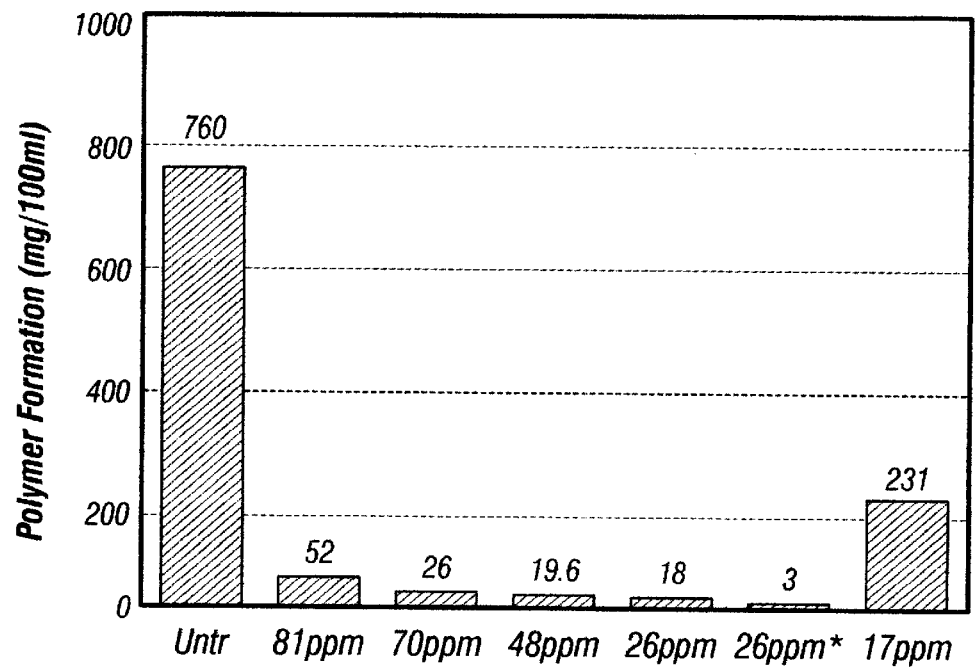
FIG. 3 is a chart showing the effect of various concentrations of BHT/UOP-5 on polymer formation.

The results are shown in FIG. 3. The BHT/UOP-5 mixture was effective in inhibiting polymerization at all concentrations tested between 26–81 ppm. The composition apparently began to lose some effectiveness at concentration levels over about 70 ppm active inhibitor. This may result in the increase of other possible side reactions of competing radical transfer mechanisms, which would decrease the overall antioxidant effectiveness of the BHT/UOP-5 mixture. Optimum dosage levels appear to lie in the range of 20–50 ppm. The most effective concentration was 26 ppm. 26 ppm of a 2.15:1 molar ratio of BHT:UOP-5 mixed in an 18.5% solution of octylamine in FINASOL 150 was the most effective of all of the solutions tested. The effectiveness decreased when the concentration was decreased to 17 ppm.

EXAMPLE 6

The following experiment was designed to compare the effectiveness of various solvents to either reduce or solubilize the small amount of material obtained when 70 ppm of a mixture of BHT/UOP-5 at a molar ratio of 2.15:1 was used to inhibit polymer formation. The identity of the material/ polymer is not certain. The procedures of Example 2 were followed using the following co-solvents in a primary solvent of FINASOL 150:

| FLASK | CO-SOLVENT |
|---|---|
| A | None; |
| B | 13% valeric acid; |
| C | 22% soybean oil; |
| D | 13% CHEMAZOLINE T-33; |
| E | 13% ALKATERGE TIV; |
| F | 18% octylamine; |
| G | 18% LUBRIZOL 2600; |
| H | 18% ethyl-(2-aminoethyl) ethanol |

Figure 4:
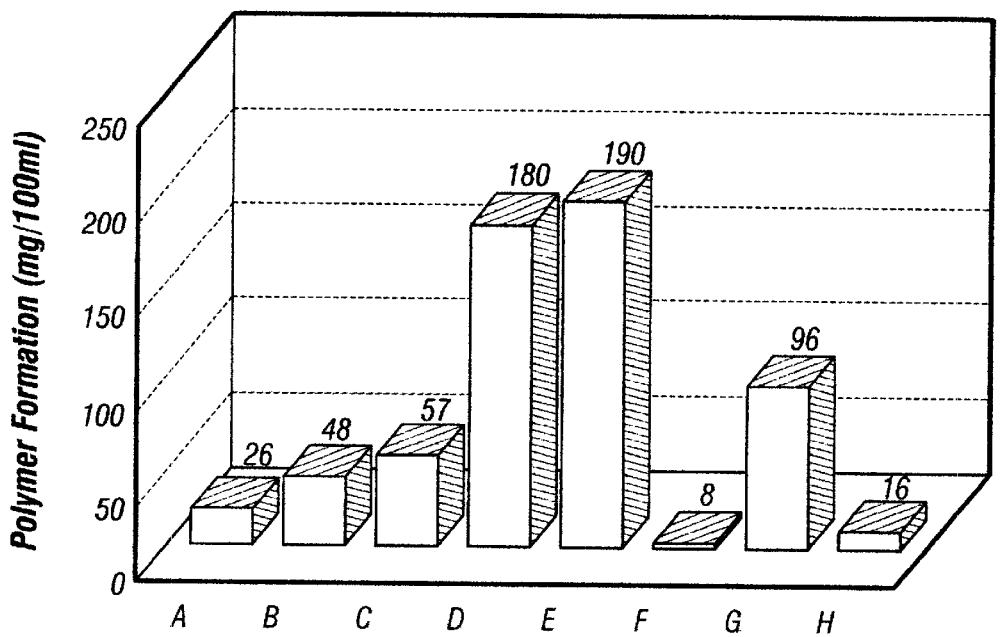
FIG. 4 is a chart showing the effect of co-solvents on the inhibition of polymerization by BHT/UOP-5.

The results are shown in FIG. 4. N-octylamine proved to be most effective cosolvent. In a repeated test, this co-solvent brought the deposit weight to virtually zero. The precise formulation for the inhibiting agent using the octylamine was:

21.85% BHT;
10.16% UOP-5;
16.1% octylamine;
51.89 FINASOL 150.

Persons of skill in the art will appreciate that many modifications may be made to the embodiments described herein without departing from the spirit of the present invention. Accordingly, the embodiments described herein are illustrative only and are not intended to limit the scope of the present invention.

We claim:

1. A reaction mixture for producing acrylonitrile comprising compounds selected from the group consisting of acrylonitrile and precursors thereof; and, a combination of a phenylenediamine and a hindered phenol at a molar ratio of at least about 2:1 and in an amount that is sufficient to inhibit polymerization of said acrylonitrile but insufficient to initiate polymerization of said acrylonitrile, wherein said hindered phenol is selected from the group consisting of 2,6di-tert-butyl phenol; 2,6-di-tert-butyl-4-methyl-phenol; 2,6-di-methyl-phenol; 2,4,6-tri-tert-butyl phenol; 2,6-di-tert-butyl-4-amine phenol; and 2,4-di-tert-butyl phenol.

2. The reaction mixture of claim 1 where the phenylenediamine comprises a para-phenylenediamine.

3. The reaction mixture of claim 1 where said phenylenediamine is selected from the group consisting of N,N'-di(nitroso)-N,N'-di(1,4-diethylpentyl)-1,4-phenylenediamine; N,N,N'-trimethyl-p-phenylenediamine; N,N,-dimethyl-p-phenylenediamine; N,N,-diethyl-p-phenylenediamine; N,N'-di-sec-butyl-p-phenylenediamine; N-phenyl-N'-dibutyl-p-phenylenediamine; N-phenyl-N'-(1,4-dimethylpentyl)-p-phenylenediamine; and N-phenyl-N'-(1,3-dimethylpentyl)-p-phenylenediamine.

4. The reaction mixture of claim 1 where said phenylenediamine is selected from the group consisting of N,N'-di(nitroso)-N,N'-di(1,4-diethylpentyl)-1,4-phenylenediamine; N-phenyl-N'-(1,4-dimethylpentyl)-p-phenylenediamine; and N,N'-di-sec-butyl-p-phenylenediamine.

5. The reaction mixture of claim 1 wherein said hindered phenol comprises 2,6-di-tert-butyl-4-methyl-phenol;

said phenylenediamine comprises N-phenyl-N'-(1,4-dimethylpentyl)-p-phenylenediamine; and wherein said ratio of hindered phenol to phenylenediamine comprises at least about 2.05:1.

6. The reaction mixture of claim 1 wherein said hindered phenol comprises 2,6-di-tert-butyl-4-methyl-phenol;

said phenylenediamine comprises N,N'-di-sec-butyl-p-phenylenediamine; and wherein said ratio of hindered phenol to phenylenediamine comprises at least about 2.15:1.

7. A reaction mixture for producing acrylonitrile comprising compounds selected from the group consisting of acrylonitrile and precursors thereof; and, a combination of a phenylenediamine and a hindered phenol at a molar ratio of at least about 2:1 and in an amount that is sufficient to inhibit polymerization of said acrylonitrile but insufficient to initiate polymerization of said acrylonitrile, wherein said hindered phenol is selected from the group consisting of 2,6-di-tert-butyl phenol; 2,6-di-tert-butyl-4-methyl-phenol; 2,6-di-methyl-phenol; 2,4,6-tri-tert-butyl phenol; 2,6-di-tert-butyl-4-amine phenol; and 2,4-di-tert-butyl phenol, where said sufficient amount of said mixture of hindered phenol and phenylenediamine comprises between about 15–75 ppm based on said reaction mixture.

8. The reaction mixture of claim 7 where said sufficient amount of said mixture of hindered phenol and phenylenediamine comprises between about 20–50 ppm based on said reaction mixture.

9. The reaction mixture of claim 7 where said phenylenediamine is selected from the group consisting of N,N'-di(nitroso)-N,N'-di(1,4-diethylpentyl)-1,4-phenylenediamine; N,N,N'-trimethyl-p-phenylenediamine; N,N,-dimethyl-p-phenylenediamine; N,N,-diethyl-p-phenylenediamine; N,N'-di-sec-butyl-p-phenylenediamine; N-phenyl-N'-dibutyl-p-phenylenediamine; N-phenyl-N'-(1,4-dimethylpentyl)-p-phenylenediamine; and N-phenyl-N'-(1,3-dimethylpentyl)-p-phenylenediamine.

10. The reaction mixture of claim 7 where said phenylenediamine is selected from the group consisting of N,N'-di(nitroso)-N,N'-di(1,4-diethylpentyl)-1,4-phenylenediamine; N-phenyl-N'-(1,4-dimethylpentyl)-p-phenylenediamine; and N,N'-di-sec-butyl-p-phenylenediamine.

11. The reaction mixture of claim 7 wherein said hindered phenol comprises 2,6-di-tert-butyl-4-methyl-phenol;

said phenylenediamine comprises N-phenyl-N'-(1,4-dimethylpentyl)-p-phenylenediamine; and wherein said ratio of hindered phenol to phenylenediamine comprises at least about 2.05:1.

12. The reaction mixture of claim 7 wherein said hindered phenol comprises 2,6-di-tert-butyl-4-methyl-phenol;

said phenylenediamine comprises N,N'-di-sec-butyl-p-phenylenediamine; and wherein said ratio of hindered phenol to phenylenediamine comprises at least about 2.15:1.

* * * * *